(12) United States Patent
Brandhorst et al.

(10) Patent No.: US 7,258,682 B2
(45) Date of Patent: Aug. 21, 2007

(54) METHOD FOR MANUFACTURING A HYPODERMIC SYRINGE WITH GLUED-IN CANULA AND HYPODERMIC SYRINGE

(75) Inventors: Erik Brandhorst, Hiddenhausen (DE); Andreas Geiger, Kirchlengern (DE)

(73) Assignee: Gerresheimer Buende GmbH, Buende (DE)

( * ) Notice: Subject to any disclaimer, the term of this patent is extended or adjusted under 35 U.S.C. 154(b) by 598 days.

(21) Appl. No.: 10/424,506

(22) Filed: Apr. 28, 2003

(65) Prior Publication Data

US 2005/0101916 A1    May 12, 2005

(30) Foreign Application Priority Data

Apr. 12, 2002    (EP) .................... 02008347

(51) Int. Cl.
*A61M 5/32*    (2006.01)
*B05D 7/22*    (2006.01)

(52) U.S. Cl. ...................... 604/265; 427/236
(58) Field of Classification Search ............. 427/2.1, 427/236, 421, 421.1; 604/265
See application file for complete search history.

(56) References Cited

U.S. PATENT DOCUMENTS

| 4,046,616 | A | * | 9/1977 | Klein | ............... 156/559 |
|---|---|---|---|---|---|
| 4,781,701 | A | * | 11/1988 | Geprags | ............... 604/240 |
| 5,456,940 | A | * | 10/1995 | Funderburk | ............... 427/2.1 |
| 5,540,666 | A | * | 7/1996 | Barta et al. | ............... 604/192 |
| 5,683,536 | A | * | 11/1997 | Kneafsey | ............... 156/327 |
| 6,093,175 | A | * | 7/2000 | Gyure et al. | ............... 604/230 |
| 2002/0012741 | A1 | * | 1/2002 | Heinz et al. | ............... 427/2.1 |
| 2002/0138042 | A1 | * | 9/2002 | Llorach et al. | ............... 604/187 |

* cited by examiner

*Primary Examiner*—Sharon E. Kennedy
(74) *Attorney, Agent, or Firm*—Laurence A. Greenberg; Werner H. Stemer; Ralph E. Locher

(57) ABSTRACT

Method for producing a syringe with a glued cannula, in which a syringe body is provided with a lubricant internally at high temperature, and either the lubricant is prevented from penetrating into a cannula receptacle of the syringe body, or the lubricant is cleared from the cannula receptacle of the syringe body afterward, and a cannula is glued into the cannula receptacle; and a syringe with a body comprising a cylinder portion and a narrowed cannula receptacle portion, whereby the cylinder portion is provided internally with a lubricant—this being deposited at high temperature—a cannula receptacle of the receptacle portion is cleared of lubricant, and a cannula is glued into the cannula receptacle.

23 Claims, No Drawings

METHOD FOR MANUFACTURING A HYPODERMIC SYRINGE WITH GLUED-IN CANULA AND HYPODERMIC SYRINGE

BACKGROUND OF THE INVENTION

Field of the Invention

The invention relates to a method for producing a syringe with a glued cannula and a syringe produced by said method.

Syringes are typically treated with a lubricant on the inside surface of the syringe body, typically by vapor-deposition or "baking" at high temperature, in order to guarantee that excess lubricant is not injected with the active substance.

A resulting problem is that, during injections with a glued cannula, the glue with which the cannula is glued into a cannula receptacle opening of the syringe body cannot endure high temperatures (e.g. 250 to 300° C.) without discoloration or destruction.

On the other hand, it is also difficult to provide a syringe body that is already treated with lubricant with a cannula, because a surface that is treated with lubricant no longer sufficiently accepts a glue.

A silicon emulsion is typically utilized for glass syringes, with which the inside surface of the syringe body is wetted, whereupon the silicon is baked in an oven at 260° C. for between 15 and 120 minutes. Silicon unavoidably gets on the inside wall of the cannula receptacle, as a result of which reliable adhesion is no longer guaranteed.

SUMMARY OF THE INVENTION

The object of the invention is to propose a technique for producing a syringe with a glued cannula in which a reliable adhesion of the cannula is possible despite the application of a lubricant at high temperature.

This object is inventively achieved by a method for fabricating a syringe with a glued cannula in which a syringe body is internally provided with a lubricant at high temperature, a cannula receptacle of the syringe body is cleared of lubricant, and a cannula is glued into the cannula receptacle.

The lubricant can be removed with the aid of a chemical solvent, by means of plasma energy, mechanically, abrasively, or by blasting (e.g. with aluminum oxide particles).

In any case, it is guaranteed that unwanted lubricant is substantially cleared, prior to the gluing process, from the inside surface of the cannula receptacle which comes in contact with the glue, so that a stable adhesion is achieved.

The object is further achieved by a method for producing a syringe with a glued cannula in which a syringe body is internally provided with a lubricant at high temperature, whereby lubricant is prevented from penetrating into a cannula receptacle of the syringe body, and a cannula is glued into said receptacle.

In this aspect of the invention, the lubricant is prevented at the outset from disadvantageously penetrating into the cannula receptacle and settling on its inside wall during the baking process. This can also be accomplished by temporarily sealing the cannula receptacle on both ends, for instance with a membrane consisting of a heat-resistant material or a stopper-shaped sealing body consisting of heat-resistant material.

Alternatively, the cannula receptacle can be provided with a flushing gas such as air, nitrogen or $CO_2$ while the syringe body is being provided with the lubricant.

According to either inventive method, it can be provided that the lubricant is vapor-deposited, or that the lubricant is applied in the form of an emulsion and baked at 250° to 300° C. Silicon can be utilized as the lubricant. A conventional non-heat-resistant glue can be utilized, for instance polyurethane methacrylate.

The invention further relates to a syringe with a body comprising a cylinder portion and a narrowed cannula receptacle portion, whereby the cylinder portion is internally provided with a lubricant which is deposited at high temperature, a cannula receptacle of the cannula receiving portion is free of lubricant, and a cannula is glued into the receptacle, whereby a conventional, non-heat-resistant glue such as polyurethane methacrylate may be utilized.

The syringe body advantageously consists of glass. The lubricant can be silicon. It is advantageously provided that the cannula receptacle is internally blasted.

DESCRIPTION OF THE PREFERRED EMBODIMENTS

An exemplifying embodiment of the invention will now be described.

Glass syringes are internally siliconized with a silicon emulsion (1%) and baked in an oven at 260° C. for 120 minutes.

After the burn-in siliconization, the baked silicon layer is removed from the cannula receptacle by a chemical technique with the aid of methylene chloride or by a mechanical technique by blasting with aluminum oxide (grain size: 2/100 mm).

During the chemical removal process, the syringes were immersed in a methylene chloride bath, with the needle receptacle entirely immersed.

After that, the cannula was glued in with a conventional glue, and the syringes were autoclaved.

Both chemically treated and mechanically treated syringes passed a cannula pull test, which means that the inventively achieved adhesion is appreciably greater than the adhesion in syringes which are siliconized by baking but do not undergo further processing.

We claim:

1. A method for producing a syringe with a glued cannula, the method which comprises:
   internally providing a syringe body with a lubricant at a high temperature;
   removing the lubricant from a cannula receptacle of the syringe body; and
   gluing a cannula into the cannula receptacle.

2. The method according to claim 1, wherein the step of removing the lubricant is performed using a chemical solvent.

3. The method according to claim 1, wherein the step of removing the lubricant is performed using plasma energy.

4. The method according to claim 1, wherein the step of removing the lubricant includes mechanically removing the lubricant.

5. The method according to claim 4, wherein the step of removing the lubricant includes removing the lubricant by abrasion.

6. The method according to claim 5, wherein the step of removing the lubricant includes removing the lubricant by blasting.

7. The method according to claim 1, wherein the lubricant is removed using methylene chloride.

8. The method according to claim 1, wherein the step of providing the syringe body with the lubricant includes vapor-depositing the lubricant.

9. The method according to claim 1, wherein the step of providing the syringe body with the lubricant includes depositing the lubricant as an emulsion and baking the lubricant at 250 to 300°C.

10. The method according to claim 9, which further comprises using silicon as the lubricant.

11. The method according to claim 1, wherein the step of gluing the cannula into the cannula receptacle is performed using a non-heat-resistant glue.

12. The method according to claim 1, wherein the step of gluing the cannula into the cannula receptacle is performed using polyurethane methacrylate.

13. The method for producing a syringe with a glued cannula, the method which comprises:
   internally providing a syringe body with a lubricant at a high temperature while preventing the lubricant from penetrating into a cannula receptacle of the syringe body; and
   gluing a cannula into the cannula receptacle.

14. The method according to claim 13, wherein the step of preventing the lubricant from penetrating into the cannula receptacle is performed by temporarily sealing the cannulLa receptacle so that the lubricant cannot penetrate into the cannula receptacle.

15. The method according to claim 14, wherein the step of sealing the cannula receptacle is performed by sealing an end of the cannula receptacle with a membrane consisting of heat-resistant material.

16. The method according to claim 14, wherein the step of sealing the cannula receptacle is performed by sealing an end of the cannula receptacle with a body consisting of a heat-resistant material; the body forming a stopper.

17. The method according to claim 13, which further comprises flushing the cannula receptacle with a gas while performing the step of providing the syringe body with the lubricant.

18. The method according to claim 13, which further comprises flushing the cannula receptacle with air, nitrogen, or carbon dioxide while performing the step of providing the syringe body with the lubricant.

19. The method according to claim 13, wherein the step of providing the syringe body with the lubricant includes vapor-depositing the lubricant.

20. The method according to claim 13, wherein the step of providing the syringe body with the lubricant includes depositing the lubricant as an emulsion and baking the lubricant at 250 to 300° C.

21. The method according to claim 20, which further comprises using silicon as the lubricant.

22. The method according to claim 13, wherein the step of gluing the cannula into the cannula receptacle is performed using a non-heat-resistant glue.

23. The method according to claim 13, wherein the step of gluing the cannula into the cannula receptacle is performed using polyurethane methacrylate.

* * * * *